(12) United States Patent
Kondo et al.

(10) Patent No.: US 8,309,493 B2
(45) Date of Patent: Nov. 13, 2012

(54) POLYPHENOL-CONTENT-INCREASING AGENT FOR PLANT

(75) Inventors: Masao Kondo, Tokyo (JP); Naomi Aiba, Tokyo (JP); Setsuko Miyanari, Tokyo (JP); Masahiro Ishizuka, Tokyo (JP); Tohru Tanaka, Tokyo (JP)

(73) Assignee: Cosmo Oil Co., Ltd., Tokyo (JP)

( * ) Notice: Subject to any disclaimer, the term of this patent is extended or adjusted under 35 U.S.C. 154(b) by 536 days.

(21) Appl. No.: 12/376,865

(22) PCT Filed: Jul. 18, 2007

(86) PCT No.: PCT/JP2007/064190
§ 371 (c)(1),
(2), (4) Date: May 11, 2009

(87) PCT Pub. No.: WO2008/018273
PCT Pub. Date: Feb. 14, 2008

(65) Prior Publication Data
US 2010/0173780 A1 Jul. 8, 2010

(51) Int. Cl.
*A01N 47/10* (2006.01)
*A01N 47/24* (2006.01)
*A01N 47/20* (2006.01)
*A01N 47/06* (2006.01)
*A01N 37/00* (2006.01)
*A01N 37/44* (2006.01)
*A01N 33/00* (2006.01)
*A01N 37/18* (2006.01)

(52) U.S. Cl. ........ 504/300; 504/302; 504/303; 504/304; 504/306; 504/313; 504/320; 504/321; 504/322; 504/326; 504/334

(58) Field of Classification Search .................. None
See application file for complete search history.

(56) References Cited

FOREIGN PATENT DOCUMENTS

| | | | |
|---|---|---|---|
| EP | 0514776 A | | 11/1992 |
| EP | 0598304 A | | 5/1994 |
| EP | 0714600 A | | 6/1996 |
| EP | 714 600 | * | 7/1996 |
| JP | 4-009360 A | | 1/1992 |
| JP | 4-338305 A | | 11/1992 |
| JP | 5-117110 A | | 5/1993 |
| JP | 7-53487 A | | 2/1995 |
| JP | 8-151304 A | | 6/1996 |
| JP | 8-225408 A | | 9/1996 |
| JP | 9-87108 A | | 3/1997 |
| JP | 2001-316255 A | | 11/2001 |
| JP | 2003-40770 A | | 2/2003 |
| JP | 2004-505105 A | | 2/2004 |
| JP | 2006-52217 A | | 2/2006 |

OTHER PUBLICATIONS

Horinaka, et al., "Luteolin induces apoptosis via death receptor 5 upregulation in human malignant tumor cells" Oncogene, 2005, vol. 24 pp. 7180-7189.
Vieira et al., "Effect of dietary phenolic compounds on apoptosis of human cultured endothelial cells induced by oxidized LDL" British Journal of Pharmacology, 1998, vol. 123, pp. 565-573.
Zhang et al., "Effect of 5-aminolevulinic acid on development and salt tolerance of potato (*Solanum tuberosum* L.) microtubers in vitro" Plant Growth Regulation 2006, vol. 49, pp. 27-34.
Extended European Search Report issued in application No. 07790944.8 dated Jan. 12, 2010.
Australian Office Action, dated Oct. 12, 2011, issued in Application No. 2007282729.
Communication from the Japanese Patent Office, dated Dec. 6, 2011, issued in counterpart Japanese Application No. 2006-217805.
Japanese Office Action dated Mar. 21, 2012, as issued in Japanese Patent Application No. 2006-217805.
Office Action dated Mar. 30, 2012 in the corresponding Korean Application No. 10-2009-7002584.
Office Action dated Aug. 12, 2011 from the Korean Intellectual Property Office in counterpart Korean application No. 10-2009-7002584.

* cited by examiner

*Primary Examiner* — Alton Pryor
(74) *Attorney, Agent, or Firm* — Sughrue Mion, PLLC

(57) ABSTRACT

To provide a polyphenol-content-increasing agent which increases the content of polyphenol in a plant.
A polyphenol-content-increasing agent for plant, containing, as an active ingredient, a 5-aminolevulinic acid or a derivative thereof represented by the following formula (1):
(Chem 1)

$$R^2R^1NCH_2COCH_2CH_2COR^3 \qquad (1)$$

wherein $R^1$ and $R^2$ each independently represents a hydrogen atom, an alkyl group, an acyl group, an alkoxycarbonyl group, an aryl group, or an aralkyl group; $R^3$ represents a hydroxyl group, an alkoxy group which may have a substituent, an acyloxy group, an alkoxycarbonyloxy group, an aryloxy group, an aralkyloxy group, or an amino group, or a salt thereof.

6 Claims, No Drawings

POLYPHENOL-CONTENT-INCREASING AGENT FOR PLANT

TECHNICAL FIELD

The present invention relates to an agent which increases the content of polyphenol contained in a plant.

BACKGROUND ART

Polyphenol is a generic term of compounds having two or more phenolic hydroxyl groups in the same molecules. The number thereof amounts to 5000 or more and it is classified into phenylcarboxylic acid-based, lignan-based, curcumin-based, coumarin-based, or flavonoid-based one. Polyphenol is a varied sugar which is changed in part, is contained in leaves, flowers, bark, and the like of plants, is synthesized by photosynthesis, and has an action of deactivating active oxygen generated by ultraviolet rays.

Lifestyle-related diseases such as cancers and cardiac diseases are developed through DNA damage, breakage of cell membranes, protein denaturalization, receptor injury and the like caused by active oxygen generated in fat-soluble components between cells and on cell membranes. Polyphenol may induce apoptosis of cancer cells and also deactivate active oxygen through the antioxidant action, so that polyphenol is said to be effective for prevention of these diseases (Non-Patent Documents 1 and 2).

Therefore, polyphenol attracts attention as an active ingredient of functional foods and studies on the search for plants containing polyphenol have been actively performed. However, an attempt to increase the content of polyphenol in a plant is hardly known and a method of increasing the content of flavonoid, which is one kind of polyphenol, using a specific acylcyclohexanedione is only disclosed in Patent Document 1 recently laid-open to public.

A series of 5-aminolevulinic acids such as 5-aminolevulinic acid represented by $NH_2CH_2CO(CH_2)_2COOH$, derivatives of its alkyl esters, etc., hydrochlorides thereof, and the like are known to be useful as a photosensitizer in photo-kinetic therapy (Patent Document 2), a plant growth regulator (Patent Document 3), a herbicide (Patent Document 4), a therapy of infection with fish pathogenic microorganisms and parasites (Patent Document 5), a pig growth accelerator (Patent Document 6), a plant oligosaccharide-increasing agent (Patent Document 7), and the like. However, a polyphenol-increasing effect thereof is entirely not known.

Patent Document 1: JP-A-2006-52217
Patent Document 2: JP-T-2004-505105
Patent Document 3: JP-A-07-53487
Patent Document 4: JP-A-05-117110
Patent Document 5: JP-A-2001-316255
Patent Document 6: JP-A-2003-40770
Patent Document 7: JP-A-09-87108
Non-Patent Document 1: Br J Pharmacol 123:565-573, (1998)
Non-Patent Document 2: Oncogene 24: 7180-7189, 2005

DISCLOSURE OF THE INVENTION

Problems that the Invention is to Solve

An object of the invention is to provide a polyphenol-content-increasing agent which increases the content of polyphenol in a plant.

Means for Solving the Problems

The present inventors have found that the content of polyphenol in a plat is increased by the use of a 5-aminolevulin in a plant and thus they have accomplished the invention.

Namely, the invention provides a polyphenol-content-increasing agent for plant, comprising, as an active ingredient, a 5-aminolevulinic acid represented or a derivative thereof by the following formula (1):
(Chem 1)

wherein $R^1$ and $R^2$ each independently represents a hydrogen atom, an alkyl group, an acyl group, an alkoxycarbonyl group, an aryl group, or an aralkyl group; $R^3$ represents a hydroxyl group, an alkoxy group which may have a substituent, an acyloxy group, an alkoxycarbonyloxy group, an aryloxy group, an aralkyloxy group, or an amino group, or a salt thereof.

Advantage of the Invention

The use of the polyphenol-content-increasing agent of the invention can increase the content of plant polyphenol conveniently and effectively and thus can impart a nature as a functional food to a plant.

BEST MODE FOR CARRYING OUT THE INVENTION

The active ingredient of the polyphenol-content-increasing agent of the invention is a 5-aminolevulinic acid or a derivative thereof represented by the above formula (1), or a salt thereof.

The alkyl group represented by $R^1$ and $R^2$ in the formula (1) is preferably a linear or branched alkyl group having 1 to 24 carbon atoms, and more preferably an alkyl group having 1 to 18 carbon atoms, particularly an alkyl group having 1 to 6 carbon atoms is preferred. As the alkyl group having 1 to 6 carbon atoms, there may be mentioned a methyl group, an ethyl group, an n-propyl group, an isopropyl group, an n-butyl group, a sec-butyl group, and the like.

As the acyl group represented by $R^1$ and $R^2$, a linear or branched alkanoyl group, alkenylcarbonyl group, aroyl group, or aryloxycarbonyl group having 1 to 24 carbon atoms, preferably 1 to 12 carbon atoms is preferred, and particularly an alkanoyl group having 1 to 6 carbon atoms is preferred. As the acyl group, there may be mentioned a formyl group, an acetyl group, an n-propanoyl group, an n-butanoyl group, an n-pentanoyl group, an n-hexanoyl group, an n-nonanoyl group, a benzyloxycarbonyl group, and the like.

As the alkoxycarbonyl group represented by $R^1$ and $R^2$, an alkoxycarbonyl group having 2 to 13 carbon atoms in total is preferred, and particularly an alkoxycarbonyl group having 2 to 7 carbon atoms is preferred. As the alkoxycarbonyl group, there may be mentioned a methoxycarbonyl group, an ethoxycarbonyl group, an n-propoxycarbonyl group, an isopropoxycarbonyl group, and the like.

As the aryl group represented by $R^1$ and $R^2$, an aryl group having 6 to 16 carbon atoms is preferred and there may be, for example, mentioned a phenyl group, a naphthyl group, and the like.

As the aralkyl group represented by $R^1$ and $R^2$, a group composed of an aryl group having 6 to 16 carbon atoms and the above alkyl group having 1 to 6 carbon atoms is preferred and there may be, for example, mentioned a benzyl group and the like.

As the alkyl group which may have substitution, the group being represented by $R^3$, there may be, for example, mentioned a linear or branched or cyclic structure-having alkyl group having 1 to 24 carbon atoms and the like which may have a substituent. As the substituent which the alkyl group may have, there may be, for example, mentioned a hydroxyl group, an alkoxy group, a phenyl group, and the like. As preferred examples of the alkyl group which may have a substituent, there may be, for example, mentioned a methyl group, an ethyl group, an n-propyl group, an isopropyl group, an n-butyl group, an isobutyl group, a tert-butyl group, an n-pentyl group, an isopentyl group, a neopentyl group, a tert-pentyl group, a 2-methylbutyl group, an n-hexyl group, a cyclohexyl group, an isohexyl group, a 3-methylpentyl group, an ethylbutyl group, an n-heptyl group, a 2-methylhexyl group, an n-octyl group, an isooctyl group, a tert-octyl group, a 2-ethylhexyl group, a 3-methylheptyl group, an n-nonyl group, an isononyl group, a 1-methyloctyl group, an ethylheptyl group, an n-dodecyl group, a 1-methylnonyl group, an n-undecyl group, a 1,1-dimethylnonyl group, an n-tridecyl group, an n-tetradecyl group, an n-pentadecyl group, an n-hexadecyl group, an n-heptadecyl group, an n-octadecyl group, a benzyl group, a phenethyl group, a 3-phenylpropyl group, a hydroxyethyl group, an ethoxyethyl group, and the like. Of these, an alkyl group having 1 to 6 carbon atoms is more preferred.

As the acyloxy group represented by $R^3$, a linear or branched alkanoyloxy group having 1 to 12 carbon atoms is preferred, and particularly, an alkanoyloxy group having 1 to 6 carbon atoms is preferred. As the acyloxy group, there may be mentioned an acetoxy group, a propionyloxy group, a butyryloxy group, and the like.

As the alkoxycarbonyloxy group represented by $R^3$, an alkoxycarbonyloxy group having 2 to 13 carbon atoms in total is preferred, and particularly, an alkoxycarbonyloxy group having 2 to 7 carbon atoms in total is preferred. As the alkoxycarbonyloxy group, there may be mentioned a methoxycarbonyloxy group, an ethoxycarbonyloxy group, an n-propoxycarbonyloxy group, an isopropoxycarbonyloxy group, and the like.

As the aryloxy group represented by $R^3$, an aryloxy group having 6 to 16 carbon atoms is preferred, and there may be, for example, mentioned a phenoxy group, a naphthyloxy group, and the like. As the aralkyloxy group, one having the above aralkyl group is preferred, and there may be, for example, mentioned a benzyloxy group and the like.

As $R^1$ and $R^2$ in the formula (1), a hydrogen atom is preferred. As $R^3$, a hydroxyl group, an alkoxy group, or an aralkyloxy group is preferred, and more preferably, a hydroxyl group or an alkoxy group having 1 to 12 carbon atoms, particularly 1 to 6 carbon atoms, in particular, a methoxy group or a hexyloxy group is preferred.

As the 5-aminolevulinic acid derivative, there may be mentioned 5-aminolevulinic acid methyl ester, 5-aminolevulinic acid ethyl ester, 5-aminolevulinic acid propyl ester, 5-aminolevulinic acid butyl ester, 5-aminolevulinic acid pentyl ester, 5-aminolevulinic acid hexyl ester, and the like. Particularly, 5-aminolevulinic acid methyl ester or 5-aminolevulinic acid hexyl ester is preferred.

As the salt of 5-aminolevulinic acid or the derivative thereof, there may be, for example, mentioned acid addition salts such as hydrochlorides, hydrobromides, hydroiodides, phosphates, methyl phosphates, ethyl phosphates, phosphites, hypophosphites, nitrates, sulfates, acetates, propionates, toluenesulfonates, succinates, oxalates, lactates, tartrates, glycolates, methanesulfonates, butyrates, valerates, citrates, fumarates, maleates, and malates; metal salts such as sodium salts, potassium salts, and calcium salts; ammonium salts, alkyl ammonium salts, and the like. These salts are used as aqueous solutions or powders at their use.

The above 5-aminolevulinic acid, a derivative thereof, and a salt thereof (hereinafter sometimes referred to as "5-aminolevulinic acid or the like") may form hydrates or solvates. Moreover, any of them may be used singly or two or more thereof may be suitably used in combination.

The 5-aminolevulinic acid or the like to be used in the invention can be produced by any method of chemical synthesis, production by a microorganism, and production by an enzyme. Specifically, it can be produced in accordance with the methods described in JP-A-48-92328, JP-A-62-111954, JP-A-2-76841, JP-A-6-172281, JP-A-7-188133, JP-A-11-42083, and the like. The 5-aminolevulinic acid or the like and a chemical reaction solution or fermentation liquid thereof before purification, which are produced as above, can be used as they are without separation and purification unless they contain harmful substance(s). Moreover, a commercial product or the like can be also used.

As shown in the following Examples, by treating a plant with 5-aminolevulinic acid or the like, the total content of chlorogenic acid, caffeic acid, ferulic acid, rutin, quercetin, luteolin, hesperetin, kaempferol, apigenin, and isorhamnetin, which are typical polyphenol contained in a plant, is increased. Therefore, 5-aminolevulinic acid or the like can be used as a polyphenol-content-increasing agent of a plant. The action of such 5-aminolevulinic acid or the like is entirely not expected and the invention is useful for improving a value of a plant as a functional food.

The increasing agent of the invention is suitably used as an increasing agent for phenylcarboxylic acid-based, lignan-based, curcumin-based, coumarin-based, or flavonoid-based polyphenol, particularly as an increasing agent for phenylcarboxylic acid-based or flavonoid-based polyphenol. Furthermore, the agent is suitably used as an increasing agent for chlorogenic acid, caffeic acid, or ferulic acid among phenylcarboxylic acid-based polyphenol and as an increasing agent for apigenin, rutin, luteolin, quercetin, kaempferol, isorhamnetin, hesperetin, or the like among flavonoid-based polyphenol.

The plant to be a target for the polyphenol-content-increasing agent of the invention is not particularly limited but, in the case where a plant having an enhanced polyphenol content is utilized as a functional food, it is advantageous to use a plant having a high polyphenol content. As such a plant, there may be, for example, mentioned plants belonging to Camelliaceae, Solanaceae, Lagminosae, Umbelliferae, Liliaceae, or Rosaceae. As a food, there may be mentioned cereals, beans, potatoes and starches, nuts and seeds, vegetables, fruits, and mushrooms. Of these, specifically, apple, pear, soybean, green soybean, parsley, strawberry, asparagus, onion, green pepper, grapes, and tea are preferred and particularly, for the purpose of increasing flavonoid-based one, pear, green soybean, green pepper, and tea are preferred. Tea is used as black tea, oolong tea, green tea, or the like.

The polyphenol-content-increasing agent of the invention is suitable as an increasing agent for particularly chlorogenic acid, ferulic acid, rutin, quercetin, or hesperetin in the case where green pepper is a target, is suitable as an increasing agent for particularly caffeic acid, ferulic acid, apigenin, or isorhamnetin in the case where pear is a target, is suitable as an increasing agent for hesperetin in the case where green soybean is a target, is suitable as an increasing agent for luteolin or hesperetin in the case where tea is a target, is suitable as an increasing agent for luteolin or hesperetin in the case where asparagus is a target, and is suitable as an increasing agent for quercetin or hesperetin in the case where parsley is a target.

As a form of the polyphenol-content-increasing agent of the invention, there may be mentioned a powder, a tablet, a granule, or the like.

They can be produced suitably using a solvent, a dispersion medium, a filler, an excipient, and/or the like in accordance with a usual method.

The polyphenol-content-increasing agent of the invention may be also used after a powder of 5-aminolevulinic acid or the like, an aqueous solution containing 5-aminolevulinic acid or the like dissolved therein, or a fermentation liquid containing 5-aminolevulinic acid or the like produced by the aforementioned method is adsorbed on a support such as an excipient. The kind of the support may be a common one and there may be mentioned crystalline cellulose, gelatin, starch, dextrin, an oil cake, baker's yeast, sake yeast, wine yeast, powdered skim milk, lactose, animal or vegetable oil and fat, anhydrous calcium phosphate, calcium carbonate, magnesium stearate, magnesium aluminosilicate, magnesium aluminometasilicate, and the like.

In the case of preparing the polyphenol-content-increasing agent of the invention as an aqueous solution, in order to prevent decomposition of 5-aminolevulinic acid or the like as an active ingredient, it is necessary to pay attention so that the aqueous solution does not become alkaline. In the case where the aqueous solution becomes alkaline, the decomposition of the active ingredient can be prevented by removing dissolved oxygen.

The polyphenol-content-increasing agent of the invention is not particularly limited so far as it contains 5-aminolevulinic acid or the like as an active ingredient. 5-Aminolevulinic acid or the like is used as it is or a plant growth regulator, a sugar, an amino acid, an organic acid, an alcohol, a vitamin, a mineral, and/or the like can be mixed unless the advantage of the invention is impaired.

As the plant growth regulator to be used herein, there may be, for example, mentioned brassinolides such as epibrassinolide, choline agents such as choline chloride and choline nitrate, indolebutyric acid, indoleacetic acid, ethichlozate agent, 1-naphthylacetamide agent, isoprothiolane agent, nicotinic acid amide agent, hydroxyisooxazole agent, calcium peroxide agent, benzylaminopurine agent, metasulfocarb agent, oxyethylene docosanol agent, ethephon agent, chlochinphonac agent, gibberellin, daminozide agent, 4-CPA agent, ancymidol agent, inabenfid agent, uniconazole agent, chiormequat agent, dikeblack agent, mefluidide agent, calcium carbonate agent, piperonyl butoxide agent, and the like.

As the sugar, there may be, for example, mentioned glucose, sucrose, xylitol, sorbitol, galactose, xylose, mannose, arabinose, madurose, ribose, rhamnose, fructose, maltose, lactose, maltotriose, and the like.

As the amino acid, there may be, for example, mentioned asparagine, glutamine, histidine, tyrosine, glycine, arginine, alanine, tryptophan, methionine, valine, proline, leucine, lysine, isoleucine, and the like.

As the organic acid, there may be, for example, mentioned formic acid, acetic acid, propionic acid, butyric acid, valeric acid, oxalic acid, phthalic acid, benzoic acid, lactic acid, citric acid, tartaric acid, malonic acid, malic acid, succinic acid, glycolic acid, glutamic acid, aspartic acid, maleic acid, caproic acid, caprylic acid, myristic acid, stearic acid, palmitic acid, pyruvic acid, α-ketoglutaric acid, and the like.

As the alcohol, there may be, for example, mentioned methanol, ethanol, propanol, butanol, pentanol, hexanol, glycerol, and the like.

As the vitamin, there may be, for example, mentioned nicotinic acid amide, vitamin B6, vitamin B12, vitamin B5, vitamin C, vitamin B13, vitamin B1, vitamin B3, vitamin B2, vitamin K3, vitamin A, vitamin D2, vitamin D3, vitamin K1, α-tocopherol, β-tocopherol, γ-tocopherol, σ-tocopherol, p-hydroxybenzoic acid, biotin, folic acid, nicotinic acid, pantothenic acid, α-lipoic acid, and the like.

As the mineral, there may be, for example, mentioned nitrogen, phosphorus, potassium, sodium, calcium, boron, nickel, selenium, manganese, magnesium, zinc, copper, iron, molybdenum, and the like.

The application of the polyphenol-content-increasing agent of the invention to a plant is not particularly limited but the agent can be to be absorbed from roots, leaves, or stems. For example, the agent may be used for foliage treatment (a foliage-treating agent) or may be used for soil treatment (a soil-treating agent). Moreover, the agent may be absorbed before a plant is planted or a cutting is planted. Furthermore, the agent may be added into water at hydroponics.

In the case where the polyphenol-content-increasing agent of the invention is used as a foliage-treating agent, it is preferred that 5-aminolevulinic acid or the like is incorporated in a concentration of 0.1 to 1000 ppm, preferably 0.5 to 500 ppm, particularly preferably 1 to 300 ppm and is used in a ratio of 10 to 1000 L, particularly 50 to 300 L per 10 are. In the case where the agent is used onto a plant such as monocotyledon to which the agent is hardly attached at its leaves, it is desirable to use a spreading agent in combination. The kind and amount of the spreading agent to be used is not particularly limited.

In the case where the polyphenol-content-increasing agent of the invention is used as a soil-treating agent, it is preferred to use 5-aminolevulinic acid or the like in a ratio of 10 to 1000 g, particularly 10 to 500 g per 10 are. In this connection, at hydroponics, it is preferred to use it in about the same amount.

In the case where there is adopted a method of absorbing 5-aminolevulinic acid or the like by dipping before planting using the polyphenol-content-increasing agent of the invention, the concentration of 5-aminolevulinic acid or the like in the dipping solution is desirably 0.001 to 10 ppm, particularly 0.01 to 5 ppm and a dipping time is desirably 1 hour to 1 week, particularly 3 hours to 1 day.

The treating method with the polyphenol-content-increasing agent of the invention, particularly timing for use, growing conditions, and the like are not particularly limited but treatment is preferably conducted at the time when the content of polyphenol in a plant is high, and a low-temperature season or a dry season is particularly preferred. Moreover, a sufficient effect is obtained by treating a plant once but the effect can be further enhanced by treating the plant twice or more times. In this case, each method described above can be combined.

The polyphenol-content-increasing agent of the invention can increase the content of polyphenol in a plant. As the method of ingesting the plant to which the invention has been applied, there may be mentioned a method of ingesting the plant as it is, a method of ingesting it as a food, a processed food, or a luxury beverage, and the like method but the method of ingestion is not particularly limited unless the method decreases polyphenol to a large extend. Moreover, it is also possible to extract polyphenol from the plant, if necessary. The method of extracting and isolating polyphenol from the plant in which the content of polyphenol is increased by the polyphenol-content-increasing agent of the invention is not particularly limited and known methods are used. For example, there may be mentioned a method where water-soluble fractions are extracted with water from the plant as it is or after processed into a form suitable for extraction by drying, finely cutting, or pulverizing the plant, to thereby roughly remove contaminants and then extraction is performed with an organic solvent such as ethyl acetate; a method of purification by column chromatography using silica gel, ODS, or the like as a support; and the like method.

EXAMPLES

The following will specifically describe the invention with reference to Examples but they are cited only for illustration and do not limited the invention.

Example 1

Two containers (length: 0.75 m, width 0.5 m) were provided and soil was placed in each of them. A Chemical fertilizer (nitrogen content:phosphorus content:potassium content=15:15:15 as mass ratio) was used as a base fertilizer and young plants of green pepper (Solanaceae, genus cayenne, race Miogi) were grown for two months according to a conventional method. Water was applied to the young plants once a day by means of a sprinkling can. Prior to one month from harvest, treatment was conducted once a week with 50 mL per container of each aqueous solution containing 0 ppm (control) or 1 ppm of 5-aminolevulinic acid hydrochloride to which a spreading agent, Approach BI (manufactured by Kao Corporation) had been added in a ratio of 0.1% by mass. After harvest, 3 g of green pepper was finely cut with scissors and a kitchen knife and then homogenized after addition of water. The homogenized one was diluted up to 6 mL with distilled water (stock solution) and the stock solution was divided into three even portions and used in the following extraction methods (1) to (3). (1) Three mL of ethyl acetate was added to 2 mL of the stock solution and the resultant one was centrifuged at 3000 rpm for 10 minutes. The supernatant was transferred to a spit tube and was evaporated to dryness with nitrogen gas while the tube was immersed in a warm bath at about 60° C. Thereto were added 200 µL of methanol and 100 µL of distilled water, thereby the volume being made 300 µL. (2) Two mL of methanol was added to 2 mL of the stock solution and the resultant one was centrifuged at 3000 rpm for 10 minutes. The supernatant was transferred to a spit tube and was evaporated to dryness with nitrogen gas while the tube was immersed in a warm bath at about 60° C. Thereto were added 200 µL of methanol and 100 µL of distilled water, thereby the volume being made 300 µL. (3) One mL of 0.1N hydrochloric acid was added to 2 mL of the stock solution and the resultant one was transferred to a plastic tube and kept in a drive-lock bath at 96.5° C. for 1 hour to effect hydrolysis. Five mL of ethyl acetate was added thereto and the resultant one was centrifuged at 3000 rpm for 10 minutes. The supernatant was transferred to a spit tube and was evaporated to dryness with nitrogen gas while the tube was immersed in a warm bath at about 60° C. Thereto were added 200 µL of methanol and 100 µL of distilled water, thereby the volume being made 300 µL. The samples from (1) to (3) were measured by high-performance liquid chromatography (HPLC) (analytical conditions: the measurement was performed at a flow rate of 1.0 mL/min at a column temperature of 40° C. using a wavelength of 350 nm, using Liquid A (80% by volume of methanol/5% by volume of acetic acid) or Liquid B (10% by volume of methanol/5% by volume of acetic acid) as an eluent, and using a column of Hichrom5C18, T898, 4.6 mm×150 mm (manufactured by LLOYD'S REGISTER QUALITY COMPANY) and each concentration was calculated based on standard solutions. In Table 1, the most highly extracted value was cited among the results measured with each of the extraction methods (1) to (3). Moreover, the sum of individual concentration of polyphenol used in this time was regarded as the total amount of polyphenol.

As shown in Table 1, the total amount of polyphenol contained in the green pepper treated with the present agent was increased 9.4 times as compared with control.

TABLE 1

| Amount of polyphenol in green pepper | | |
|---|---|---|
| | ALA treatment | Control |
| Chlorogenic acid | 4856 | 675 |
| Caffeic acid | 276 | 113 |
| Ferulic acid | 5680 | 417 |
| Rutin | 5696 | 79 |
| Quercetin | 28919 | 2811 |
| Luteolin | 644 | 127 |
| Hesperetin | 236 | 0 |
| Kaempferol | 668 | 195 |
| Apigenin | 0 | 0 |
| Isorhamnetin | 1849 | 787 |
| Total amount of polyphenol | 48824 | 5204 |
| ALA/control ratio | 9.4 | — | unit: ng/g

Example 2

Prior to 150 days from harvest, treatment to pear (Camelliace, genus pear, race Kosui) grown in a production farm field was conducted once a fortnight with a spraying amount of 300 L/tan of each aqueous solution containing 0 ppm (control) or 3 ppm of 5-aminolevulinic acid hydrochloride to which a spreading agent, Approach BI (manufactured by Kao Corporation) had been added in a ratio of 0.1% by mass. After harvest, the content of polyphenol was analyzed by HPLC in the same manner as in Example 1. The results are shown in Table 2. As shown in Table 2, the total amount of polyphenol contained in the pear treated with the present agent was increased 2.3 times as compared with control.

TABLE 2

| Amount of polyphenol in pear | | |
|---|---|---|
| | ALA treatment | Control |
| Chlorogenic acid | 1819 | 6212 |
| Caffeic acid | 8400 | 838 |
| Ferulic acid | 12456 | 2337 |
| Rutin | 1595 | 1021 |
| Quercetin | 111 | 64 |
| Luteolin | 61 | 59 |
| Hesperetin | 81 | 160 |
| Kaempferol | 18 | 173 |
| Apigenin | 95 | 0 |
| Isorhamnetin | 567 | 0 |
| Total amount of polyphenol | 25202 | 10863 |
| ALA/control ratio | 2.3 | — | unit: ng/g

Example 3

Prior to 210 days from harvest, treatment to green soybean Leguminosae, genus soybean, race Hakusan) grown in a production farm field was conducted once a fortnight after flowering with a spraying amount of 100 L/tan of each aqueous solution containing 0 ppm (control) or 1 ppm of 5-aminolevulinic acid hydrochloride. After harvest, the content of polyphenol was analyzed by HPLC in the same manner as in Example 1. The results are shown in Table 3. As shown in Table 3, the total amount of polyphenol contained in the green soybean treated with the present agent was increased 1.4 times as compared with control.

TABLE 3

Amount of polyphenol in green soybean

|  | ALA treatment | Control |
|---|---|---|
| Chlorogenic acid | 17 | 45 |
| Caffeic acid | 0 | 0 |
| Ferulic acid | 3963 | 3133 |
| Rutin | 1032 | 1378 |
| Quercetin | 261 | 450 |
| Luteolin | 19 | 28 |
| Hesperetin | 1841 | 0 |
| Kaempferol | 0 | 10 |
| Apigenin | 11 | 8 |
| Isorhamnetin | 0 | 12 |
| Total amount of polyphenol | 7143 | 5064 |
| ALA/control ratio | 1.4 | — | unit: ng/g

Example 4

Prior to 210 days from harvest, treatment to tea (Camelliaceae, genus camellia, race Yabukita) grown in a production farm field was conducted once a month with a spraying amount of 100 L/tan of each aqueous solution containing 0 ppm (control) or 3 ppm of 5-aminolevulinic acid hydrochloride. After harvest, the content of polyphenol was analyzed by HPLC in the same manner as in Example 1. The results are shown in Table 4. As shown in Table 4, the total amount of polyphenol contained in the tealeaf treated with the present agent was increased 1.1 times as compared with control.

TABLE 4

Amount of polyphenol in tealeaf

|  | ALA treatment | Control |
|---|---|---|
| Chlorogenic acid | 3474 | 5245 |
| Caffeic acid | 0 | 0 |
| Ferulic acid | 17172 | 18976 |
| Rutin | 4519 | 30105 |
| Quercetin | 8249 | 1997 |
| Luteolin | 2181 | 29 |
| Hesperetin | 25887 | 0 |
| Kaempferol | 970 | 1553 |
| Apigenin | 915 | 974 |
| Isorhamnetin | 3881 | 1022 |
| Total amount of polyphenol | 67248 | 59901 |
| ALA/control ratio | 1.1 | — | unit: ng/g

Example 5

Prior to 150 days from harvest, treatment to tetraennial-root asparagus (Liliaceae, genus asparagus, race Welcome) grown in a vertical stem form in a greenhouse was conducted once a fortnight with a spraying amount of 100 L/tan of each solution containing 0 ppm (control) or 3 ppm of 5-aminolevulinic acid hydrochloride. After harvest, the content of polyphenol was analyzed in the same manner as in Example 1. The results are shown in Table 5. As shown in Table 5, the total amount of polyphenol contained in the asparagus treated with the present agent was increased 2.3 times as compared with control.

TABLE 5

Amount of polyphenol in asparagus

|  | ALA treatment | Control |
|---|---|---|
| Chlorogenic acid | 2983 | 2453 |
| Caffeic acid | 0 | 0 |
| Ferulic acid | 9899 | 7988 |
| Rutin | 40234 | 20315 |
| Quercetin | 5533 | 2083 |
| Luteolin | 1923 | 182 |
| Hesperetin | 20198 | 225 |
| Kaempferol | 723 | 887 |
| Apigenin | 456 | 598 |
| Isorhamnetin | 1022 | 998 |
| Total amount of polyphenol | 82971 | 35729 |
| ALA/control ratio | 2.3 | — | unit: ng/g

Example 6

Two containers (length: 0.75 m, width 0.5 m) were provided and soil was placed in each of them. A Chemical fertilizer (nitrogen content:phosphorus content:potassium content=15:15:15 as mass ratio) was used as a base fertilizer and seeds of parsley (Umbelliferae, genus parsley, race Paramount) were planted according to a conventional method and water was applied once a day by means of a sprinkling can. Prior to one month from harvest, treatment was conducted once a week with 50 mL per container of each aqueous solution containing 0 ppm (control) or 1 ppm of 5-aminolevulinic acid hydrochloride. After harvest, the content of polyphenol was analyzed in the same manner as in Example 1. The results are shown in Table 6. As shown in Table 6, the total amount of polyphenol contained in the parsley treated with the present agent was increased 3.5 times as compared with control.

TABLE 6

Amount of polyphenol in parsley

|  | ALA treatment | Control |
|---|---|---|
| Chlorogenic acid | 20820 | 16255 |
| Caffeic acid | 4240 | 3050 |
| Ferulic acid | 0 | 0 |
| Rutin | 28977 | 29213 |
| Quercetin | 37699 | 0 |
| Luteolin | 2733 | 1172 |
| Hesperetin | 110685 | 225 |
| Kaempferol | 10321 | 9007 |
| Apigenin | 1099 | 760 |
| Isorhamnetin | 4388 | 2716 |
| Total amount of polyphenol | 220962 | 62398 |
| ALA/control ratio | 3.5 | — | unit: ng/g

Example 7

Two containers (length: 0.75 m, width 0.5 m) were provided and soil was placed in each of them. A Chemical fertilizer (nitrogen content:phosphorus content:potassium content=15:15:15 as mass ratio) was used as a base fertilizer and young plants of pepper (Solanaceae, genus cayenne, race Habanero) were planted according to a conventional method and water was applied once a day by means of a sprinkling can. Prior to one month from harvest, treatment was conducted once a week with 50 mL per container of each aqueous solution containing 0 ppm (control) or 1 ppm of 5-aminolevulinic acid hydrochloride. After harvest, the content of polyphenol was analyzed in the same manner as in Example 1. The results are shown in Table 7. As shown in Table 7, the total amount of polyphenol contained in the pepper treated with the present agent was increased 1.4 times as compared with control.

TABLE 7

Amount of polyphenol in pepper

| | ALA treatment | Control |
|---|---|---|
| Chlorogenic acid | 18020 | 10829 |
| Caffeic acid | 5520 | 5518 |
| Ferulic acid | 9270 | 6731 |
| Rutin | 457080 | 332108 |
| Quercetin | 26700 | 21905 |
| Luteolin | 62060 | 45610 |
| Hesperetin | 0 | 12 |
| Kaempferol | 0 | 0 |
| Apigenin | 2570 | 1438 |
| Isorhamnetin | 270 | 166 |
| Total amount of polyphenol | 581490 | 424317 |
| ALA/control ratio | 1.4 | — | unit: ng/g

While the invention has been described in detail and with reference to specific embodiments thereof, it will be apparent to one skilled in the art that various changes and modifications can be made therein without departing from the spirit and scope thereof.

The present application is based on Japanese Patent Application No. 2006-217805 filed on Aug. 10, 2006, and the contents are incorporated herein by reference.

Industrial Applicability

According to the present invention, there can be provided a polyphenol-content-increasing agent which increases the content of polyphenol in a plant.

The invention claimed is:

1. A method for increasing the content of polyphenol in a plant, which comprises treating said plant with an effective amount of a 5-aminolevulinic acid or a derivative thereof represented by the following formula (1):

$$R^2R^1NCH_2COCH_2CH_2COR^3 \qquad (1)$$

wherein $R^1$ and $R^2$ each independently represents a hydrogen atom, an alkyl group, an acyl group, an alkoxycarbonyl group, an aryl group, or an aralkyl group; $R^3$ represents a hydroxyl group, an alkoxy group which may have a substituent, an acyloxy group, an alkoxycarbonyloxy group, an aryloxy group, an aralkyloxy group, or an amino group, or a salt thereof, wherein the plant is selected from the group consisting of peppers, pear, and, parsley.

2. The method for increasing the content of polyphenol in a plant according to claim 1, wherein the polyphenol is phenylcarboxylic acid-based, lignan-based, curcumin-based, coumarin-based, or flavonoid-based.

3. The method for increasing the content of polyphenol in a plant according to claim 2, wherein the phenylcarboxylic acid-based polyphenol is chlorogenic acid, caffeic acid, or ferulic acid.

4. The method for increasing the content of polyphenol in a plant according to claim 2, wherein the flavonoid-based polyphenol is apigenin, rutin, luteolin, quercetin, kaempferol, isorhamnnetin, or hesperetin.

5. The method for increasing the content of polyphenol in a plant according to any one of claim 1, 3 or 4, wherein 5-aminolevulinic acid or a derivative thereof is absorbed from leafs, stems, or roots.

6. The method for increasing the content of polyphenol in a plant according to claim 2, wherein 5-aminolevulinic acid or a derivative thereof is absorbed from leafs, stems, or roots.

* * * * *

UNITED STATES PATENT AND TRADEMARK OFFICE
CERTIFICATE OF CORRECTION

PATENT NO. : 8,309,493 B2  
APPLICATION NO. : 12/376865  
DATED : November 13, 2012  
INVENTOR(S) : Masao Kondo et al.

Page 1 of 1

It is certified that error appears in the above-identified patent and that said Letters Patent is hereby corrected as shown below:

On the Title page, after "(65) Prior Publication Data" and before "(51) Int. Cl.", insert -- (30)          Foreign Application Priority Data

Aug. 10, 2006   (JP) .................................2006-217805 --.

Signed and Sealed this  
Fifth Day of February, 2013

Teresa Stanek Rea  
*Acting Director of the United States Patent and Trademark Office*